United States Patent
Possin et al.

(10) Patent No.: US 7,283,609 B2
(45) Date of Patent: Oct. 16, 2007

(54) CT DETECTOR PHOTODIODE HAVING MULTIPLE CHARGE STORAGE DEVICES

(75) Inventors: George E. Possin, Niskayuna, NY (US); Jonathan D. Short, Saratoga Springs, NY (US); Wen Li, Clifton Park, NY (US)

(73) Assignee: General Electric Company, Niskayuna, NY (US)

(*) Notice: Subject to any disclaimer, the term of this patent is extended or adjusted under 35 U.S.C. 154(b) by 0 days.

(21) Appl. No.: 11/164,101

(22) Filed: Nov. 10, 2005

(65) Prior Publication Data

US 2007/0104311 A1 May 10, 2007

(51) Int. Cl.
*G01N 23/083* (2006.01)
*H05G 1/64* (2006.01)
*G01T 1/24* (2006.01)
*H01L 27/14* (2006.01)

(52) U.S. Cl. .................. 378/19; 378/98.8; 250/370.09; 250/370.11

(58) Field of Classification Search ............... 378/98.8, 378/19; 250/370.09, 370.11
See application file for complete search history.

(56) References Cited

U.S. PATENT DOCUMENTS

| | | | | |
|---|---|---|---|---|
| 5,218,533 | A * | 6/1993 | Schanen | 378/9 |
| 5,592,523 | A * | 1/1997 | Tuy et al. | 378/19 |
| 5,661,309 | A * | 8/1997 | Jeromin et al. | 250/580 |
| 2004/0013232 | A1* | 1/2004 | Rahn | 378/98.8 |
| 2004/0251421 | A1* | 12/2004 | Kobayashi et al. | 250/370.09 |

* cited by examiner

*Primary Examiner*—Edward J. Glick
*Assistant Examiner*—Anastasia S. Midkiff
(74) *Attorney, Agent, or Firm*—Jean K. Testa; Curtis B. Brueske

(57) ABSTRACT

A CT detector includes a pixel having a single photodiode and multiple charge storage devices that are alternately stored and read out. The photodiode is a frontlit diode with a pair of capacitors that alternately store charge generated during data acquisition. Multiple pixels are connected to a single readout amplifier. Charge is continuously acquired from each photodiode and stored on the charge storage devices, but such readout is from a single charge storage device at a time. As such, each charge storage device is read out independently, but the charge storage devices are connected to a common readout channel or port.

8 Claims, 6 Drawing Sheets

CT DETECTOR PHOTODIODE HAVING MULTIPLE CHARGE STORAGE DEVICES

BACKGROUND OF THE INVENTION

The present invention relates generally to diagnostic imaging and, more particularly, to a detector assembly for radiographic imaging having photodiodes with multiple charge storage devices. The multiple charge storage devices not only reduce the likelihood of detector saturation, but also support intraview x-ray source wobble.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Each detector element is characterized by a scintillator cell that releases light in response to the reception of x-rays. The light is collected by a photodiode, which provides an electrical signal output that is indicative of the x-rays impinged by the scintillator cell. Charge generated from the sensed light is then transmitted to a data acquisition system (DAS), either directly, or through a FET switch array. As CT detectors have become larger in z-coverage and finer pitch to improve resolution, a much larger number of interconnects are needed to connect the increasing number of photodiodes to the DAS. The most commonly practiced CT detectors include thousands of detector elements and, as a result, a comparable number of connections to a comparable number of detector elements share a common DAS input channel. Other known detectors provide charge storage at each pixel and share a single amplifier among many pixels. For example, one known detector utilizes a single DAS channel for each photodiode pixel. Other known detectors have been constructed such that as many as eight pixels connected in parallel to a single DAS channel. Connecting the photodiode pixels in parallel, however, degrades the resolution and is thus undesirable. In another known detector design, storage capacitors and FET switches are provided at each pixel. This construction is often referred to as a storage diode design. With such a design, the storage capacitor is often provided by the native capacitance of the photodiode itself. While such a construction does allow for one amplifier to be shared among many pixels, and each pixel is read individually so as not to degrade resolution, it does not permit so-called source "wobble". Source wobble requires that that the integrated signal at each pixel be sampled over the same time interval. This is not possible with the conventional storage diode detector design.

Therefore, it would be desirable to have a CT detector with a multi-charge storage device pixels as well as a CT detector whose pixels are connected in a way that multiple pixels can share a readout channel as well as support source wobble

BRIEF DESCRIPTION OF THE INVENTION

The present invention is directed to an array of pixels for a CT detector that overcomes the aforementioned drawbacks. Each pixel is designed to have multiple charge storage devices.

A CT detector pixel includes a photosensitive device, preferably a photodiode, and multiple charge storage devices that are alternately charged and readout, preferably on a per-view basis. The photodiode is preferably a frontlit diode and the charge storage devices are a pair of capacitors that alternately store charge generated by the photosensitive device. The charge storage is controlled by FET switches and associated electronics of the pixel structure. Charge from the photodiode is continuously transferred to one of the selected charge storage device. The stored charge is readout at a later time. As such, each charge storage device is read out independently, but multiple charge storage devices from multiple detector pixels are connected to a common readout channel or port. Thus, the number of readout channels could be the same despite the increased number of charge storage devices In one preferred embodiment, data acquisition is segmented into a number of sequential views. In this regard, the photo-induced charge during, for example, the odd numbered views is stored on one charge storage device and the photo-induced charge of the even numbered views is stored on the other charge storage device. During the even numbered views, the charge stored on the first charge storage device is transmitted to a DAS. In the odd numbered views, the charge stored on the second charge storage device is transmitted to the DAS and charge is stored on the first charge storage device. This alternating in charging and readout is continued throughout data acquisition. A view is defined as the time period during which photocharge is detected by each pixel element and said charge is transferred to one of the capacitors. At the end of the view period, the pixel switches are electrically reconfigured and charge is transferred to the other pixel capacitor.

Therefore, in accordance with one aspect, the invention includes an array of pixels. Each pixel comprises, in part, a photodiode functioning as a light conversion element designed to convert light released by a scintillator to electrical charge. The pixel also has a first charge storage capacitor device connected to the single light conversion element that stores electrical charge during a first acquisition and a second charge storage device different from the first charge storage device and connected to the single light conversion element that stores electrical charge during a second acquisition. In a further aspect, at any one time, only one of the two charge storage devices is selected by switches (such as FET switches) and connected to the single light conversion element.

In accordance with another aspect of the invention, a CT detector is presented as having a scintillator to release light at an intensity in response to the reception of x-rays. The CT detector further has a photodiode to provide an electrical signal indicative of the intensity of the light released by the scintillator. The photodiode has a light collection surface and a pair of capacitors for storing charge generated by the light collection surface.

According to another aspect, the invention includes a CT system having an x-ray source and an x-ray detector composed of an array of pixels. Each detector includes a plurality of scintillators arranged to release light to of the array of pixels. Each pixel has a first and a second charge storage device. The CT system further has a DAS channel connected to receive electrical signals from the array of pixels. A controller is provided to alternately connect the first and the second charge storage devices of each of the plurality of pixels to the DAS channel such that only one of the first and the second charge storage devices of each pixel transfers charge to the DAS channel for readout at any one time.

In accordance with yet another aspect of the present invention, a method of CT imaging is presented and includes the steps of defining data acquisition into a number of views and, for each view, acquiring CT data at a first x-ray source position and a second x-ray source position wobbled from the first x-ray source position. The method further includes the step of integrating charge on a first charge storage device of each pixel in an array of pixels during data acquisition with the x-ray source at the first x-ray source position as well as the step of integrating charge on a second charge storage device of each pixel during image acquisition with the x-ray source at the second x-ray source position.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the present invention is described with respect to a four-slice computed tomography (CT) system. However, it will be appreciated by those skilled in the art that the present invention is equally applicable for use with single-slice or other multi-slice configurations. The present invention will be described with respect to a "third generation" CT scanner, but is equally applicable with other CT systems.

Figure 1:
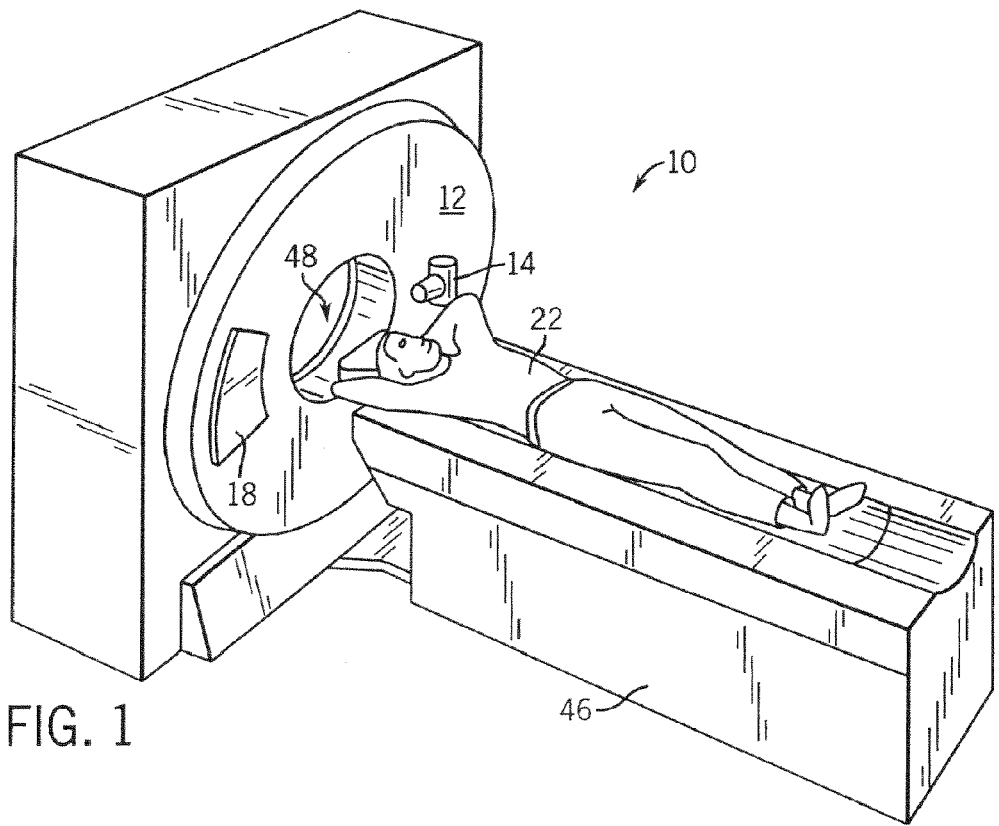
FIG. 1 is a pictorial view of a CT imaging system.
Figure 2:
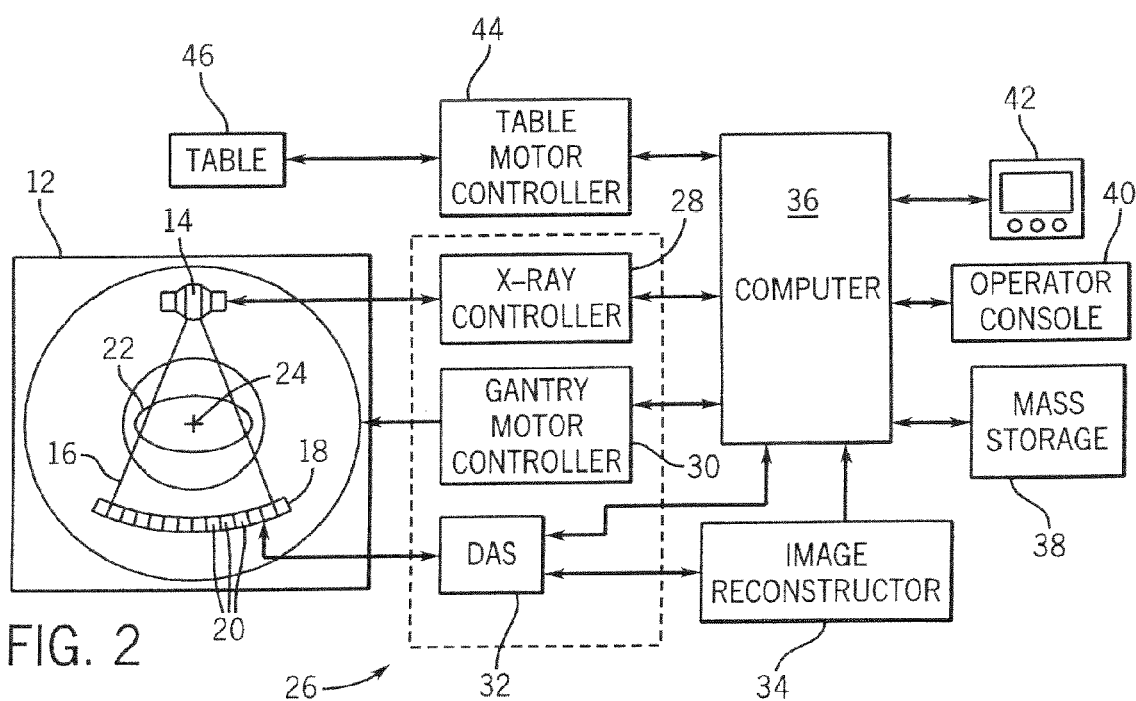
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a fan beam of x-rays 16 toward a detector array 18 on the opposite side of the gantry 12. Detector array 18 is formed by a plurality of detector modules 20 which together sense the projected x-rays that pass through a medical patient 22. Each detector module 20 comprises an array of pixel elements (pixels). Each pixel comprises in part a photosensitive element, such as a photodiode, and one or more charge storage devices, such as capacitors. Each pixel produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38. The DAS may also send signals to the detector to operate FET switches, provide bias voltages to the detector and the like.

Computer 36 also receives commands and scanning parameters from an operator via console 40 that has a keyboard. An associated display 42 allows the operator to observe the reconstructed image and other data from computer 36. The operator supplied commands and parameters that are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figure 3:
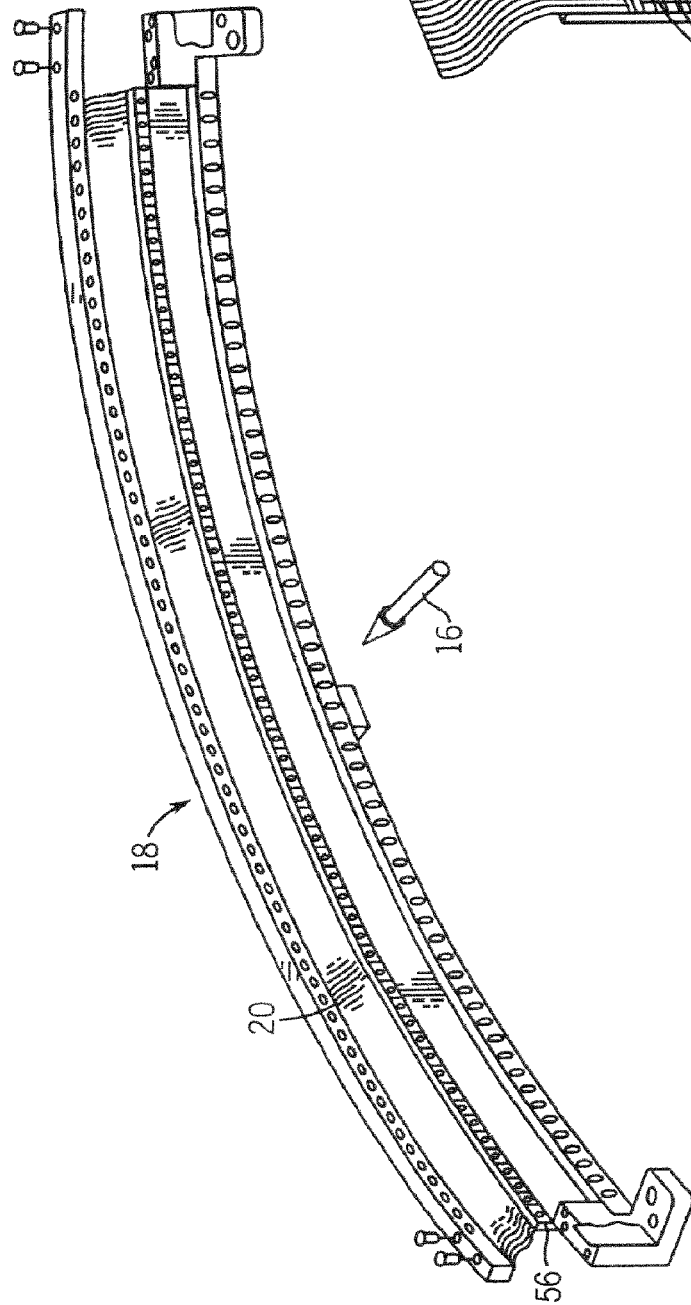
FIG. 3 is a perspective view of a CT system detector array.
Figure 4:
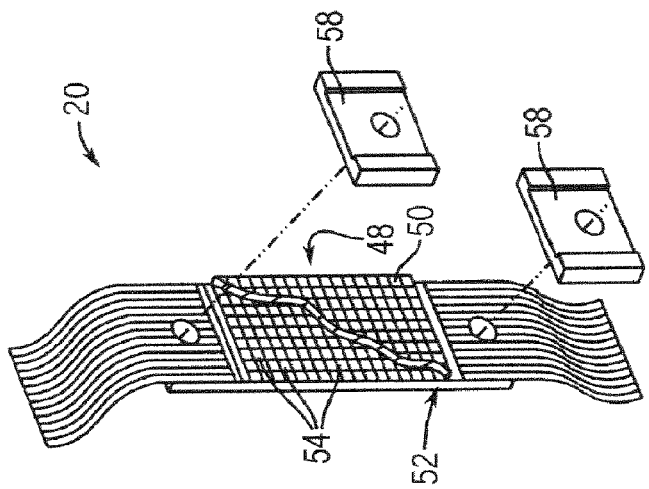
FIG. 4 is a perspective view of a detector.

As shown in FIGS. 3 and 4, detector array 18 includes a plurality of detector modules 20. A collimator (not shown) is positioned above the plurality of detector modules to collimate x-ray beams 16 before such beams impinge upon the detector modules. In one embodiment, shown in FIG. 3, detector array 18 includes 57 detector modules 20, each detector module 20 having a pixel array size of 16×16. As a result, array 18 has 16 rows and 912 columns (16×57 detectors) which allows 16 simultaneous slices of data to be collected with each rotation of gantry 12. Each detector module 20 includes a scintillator array 48 comprising a plurality of scintillators 50 that illuminate upon the reception of x-rays. Each detector module 20 also includes a pixel array 52 collectively formed of a plurality of pixels 54. As referenced above, each pixel 54 includes a photosensitive element and one or more charge storage elements. Each detector module 20 is secured to a detector frame 56, FIG. 3, by mounting brackets 58.

The present invention is directed to a CT detector having a photodiode with multiple charge storage devices, e.g., capacitors, that may be incorporated into a detector array, such as that described above, and incorporated into a CT system such as that illustrated in FIGS. 1-2 or other radiographic system. The photodiode, is preferably of frontlit construction, and includes a pair of capacitors built onto a light collection surface thereof. Moreover, when one capacitor is being charged, the other capacitor is either in a static mode holding the charge or in a readout state. In the readout state the capacitor is connected to a charge readout device such as a charge amplifier. This alternating of charging and readout is continued throughout data acquisition.

Figure 5:
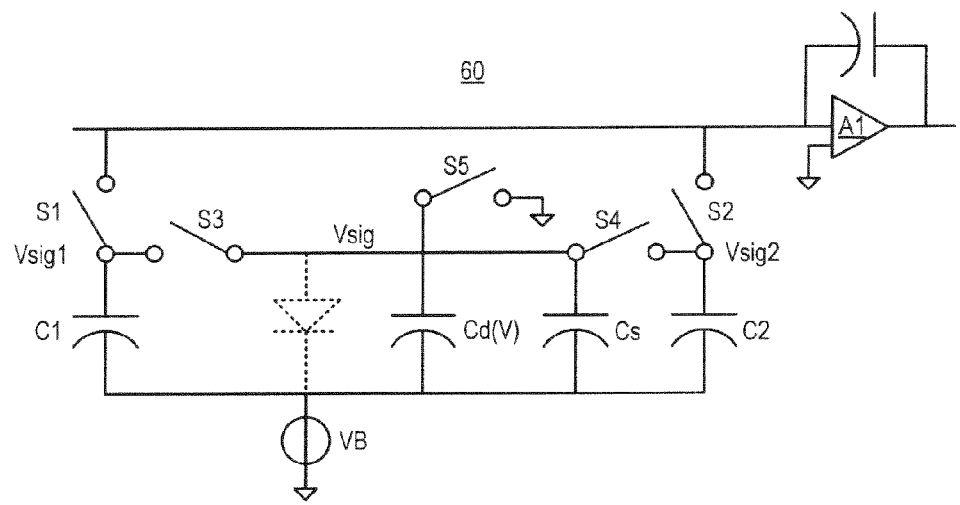
FIG. 5 is circuit schematic of a pixel having multiple charge storage devices according to one aspect of the present invention.

FIG. 5 is circuit schematic of a single pixel having multiple charge storage devices according to the present invention. One skilled in the art will readily appreciate that the circuit 60 and the components associated therewith illustrates one exemplary embodiment of the invention and that other circuits and/or components may be equivalently used. Circuit 60 includes a first capacitor C1 and a second capacitor C2, a photodiode, as well as switches S1-S5. As will be described, switches S1-S5, which preferably comprise FETs, regulate the capacitors between charging, readout, and reset states. In this regard, the switches S1 and S2 selectively connect each capacitor to readout amplifier A1. As such, both capacitors C1 and C2 share a common readout port. Circuit 60 may also include a reset switch S5 that is used to selectively reset capacitors C1 and or C2 or just the diode capacitance represented by Cd(V) between views. It should be appreciated that a multiple of pixel circuits (not shown) can also be connected to amplifier A1. If only one switch S1 or S2 in only one of the multiple of pixel circuits is closed at a time, there will be no interference between the readout of the signal from individual pixel storage capacitors.

Operation of the circuit will now be described. Switch S5 is normally open. During a first acquisition, switch S3 is closed and switches S1, S2, and S4 are opened. As a result, charge generated by the photodiode is integrated on capacitor C1. During this first acquisition, no charge is integrated on capacitor C2 as a result of switch S4 being open. After collection of data for the first acquisition view, switch S3 is opened and switch S4 is closed to begin acquisition of charge on the second capacitor C2 for the second view. During the acquisition of charge during the second view, switch S1 is closed to transmit the charge collected in capacitor C1 to the readout amplifier A1. After completion of the second acquisition, switch S4 is opened. Thereafter, switch S2 is closed to send charge stored in capacitor C2 to the DAS. For remaining acquisitions, the above switching algorithm is repeated so that capacitors C1 and C2 alternately store charge and are read out.

Figure 6:
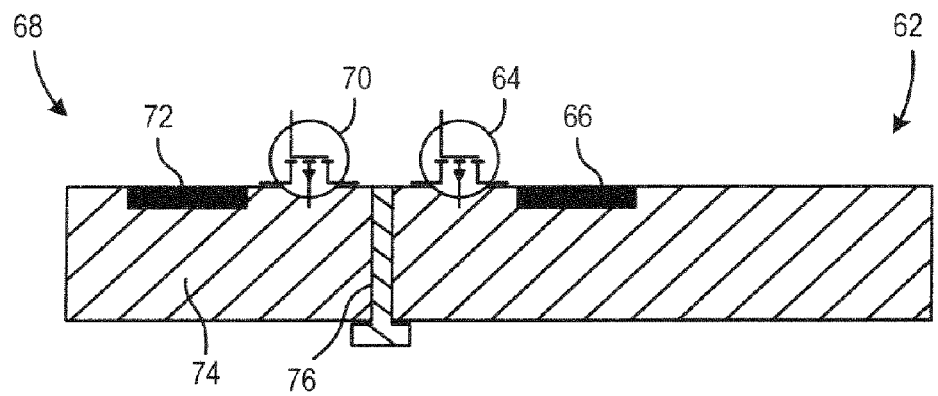
FIG. 6 is a schematic view of a pixel according to one aspect of the invention.

Referring now to FIG. 6, two pixels according to one aspect of the present invention are schematically shown. Pixel 62 is comprised in part of FET switch 64 and the remaining photodiode, capacitors, and switches are shown schematically as element 66. The second pixel 68 is similarly constructed to include FET 70 and element 72. In FIG. 6, FET 64 is equivalent to switch S1 or S2 in the circuit of FIG. 5 and FET 70 would be equivalent to the other of switch S1 or S2 in the circuit of FIG. 5. For simplicity, the other switches and other elements are not shown in the cross-section. It should be understood by those skilled in the art that all of the circuit elements shown in FIG. 5 can be constructed using standard semiconductor processing and within and on semiconductor substrate 74. FIG. 6 shows one preferred embodiment where the connections between switches S1 and S2 and the DAS amplifiers (e.g., A1) are by a conductive connection 76 through the silicon substrate 74.

The arrangement shown in FIG. 6 illustrates one embodiment of the invention. Specifically, interconnect 76, often called a through-via interconnect, routes the charge from the capacitors through the thickness of substrate 74. In this regard, the photodiode advantageously has low electronic noise per acquisition view because the parasitic capacitance between the pixel and the amplifier is reduced. Moreover, the thru-via interconnect 76 supports tiling of photodiodes into 2D arrays, which is particularly advantageous for wide coverage detectors.

Figure 7:
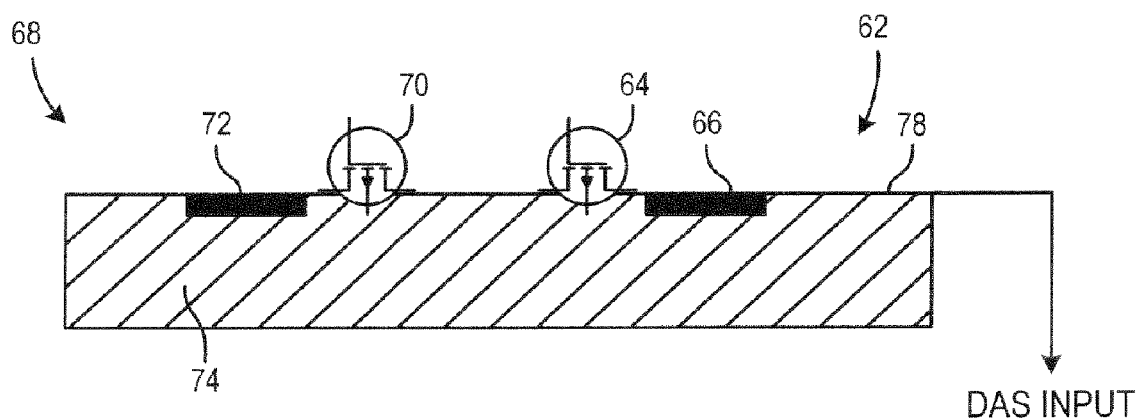
FIG. 7 is a schematic view of a pixel according to another aspect of the present invention.

Referring now to FIG. 7, a photodiode according to another embodiment of the present invention is shown. In this exemplary embodiment charge is routed from the FET switches 64, 70 by interconnect traces on the surface 78 of the detector array, to the edge of the array and thus to the DAS amplifiers.

As described herein, each photodiode of a CT detector photodiode array includes a pair of capacitors that are alternately charged and read out. In one embodiment, this alternation is coordinated with the several views defined within a single gantry rotation. That is, for one view, one of the capacitors has charge integrated thereon. For the next view, the other capacitor has charge integrated thereon. In accordance with this embodiment, for a gantry rotation defined to have 1000 views, one capacitor will have charge integrated thereon for 500 views and the other capacitor will have charge integrated thereon for the other 500 views.

However, in accordance with another embodiment of the present invention, each view is partitioned into a pair of view segments. Each view segment is defined by a unique x-ray source position for the given view. In this regard, charge is integrated during a given view on one capacitor for data acquisition with the x-ray source situated at a first x-ray source position. The x-ray source, for the given view, is then wobbled to a new or second x-ray source position. At this new x-ray source position, the other capacitor of each photodiode is then used for charge collection. As a result, both capacitors have charge integrated thereon at each view, however, one capacitor stores charge collected with the x-ray source at one position and the other capacitor stores charge associated with the x-ray source wobbled to a new x-ray source position. Thus, for a 1000 view acquisition, each capacitor will store charge for 1000 views, but each capacitor will store charge associated with a different x-ray source position.

Figure 8:
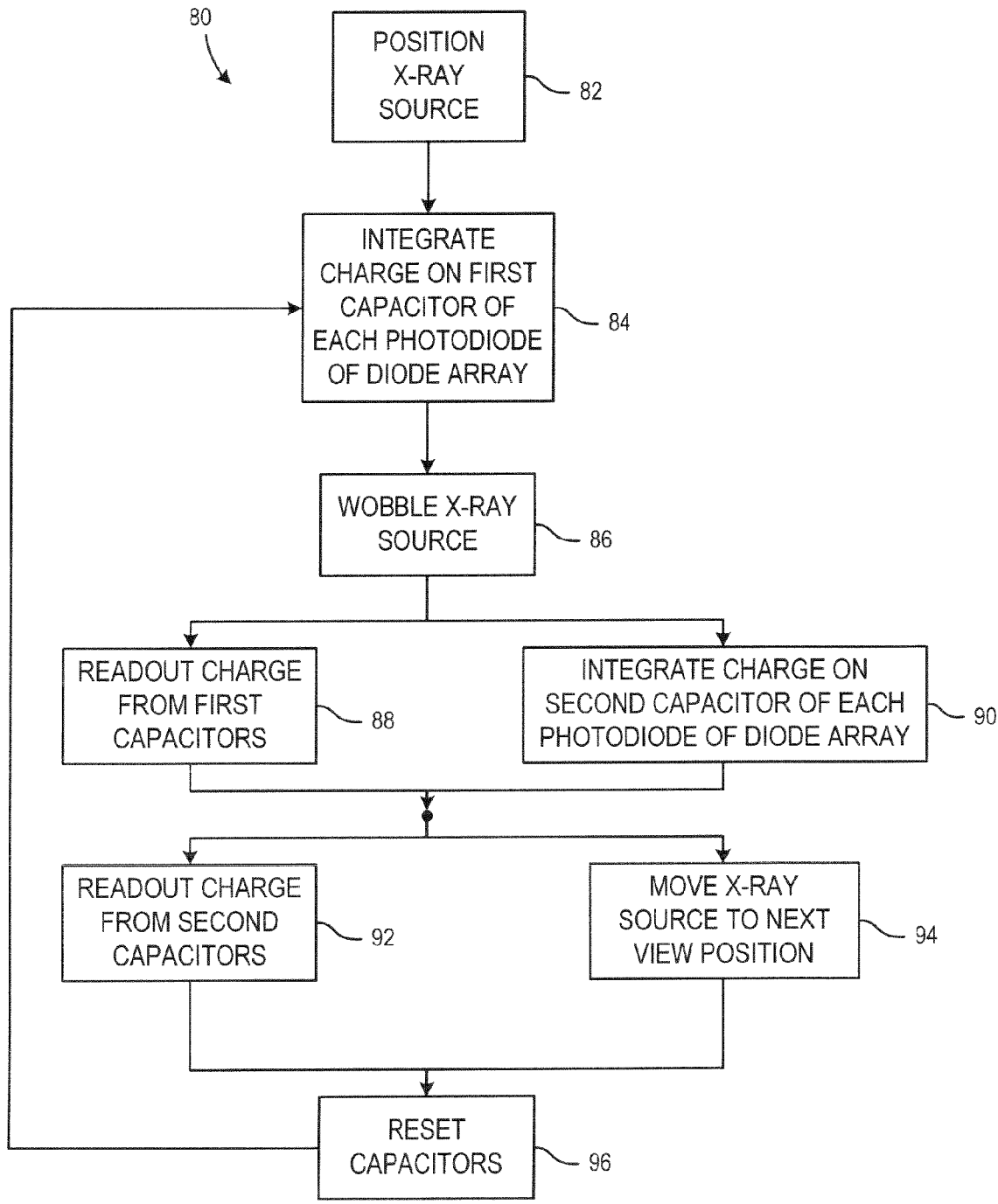
FIG. 8 is a flow chart setting forth the steps of an imaging process according to one aspect of the present invention.

Accordingly, referring now to FIG. 8, an imaging process according to a preferred embodiment of the present invention is illustrated. Process 80 begins at 82 with the x-ray source positioned for a given view acquisition. At this x-ray source position, charge is integrated on a first capacitor of each photodiode of a diode array 84. After data collection at this x-ray source position, the x-ray source is wobbled at 86 to a new x-ray source position. However, the data to be collected at this new "wobbled" position still corresponds to the same view for which data was collected at 84. With the x-ray source wobbled to its new x-ray source position 86, the charge stored in the first capacitors is read out at 88. Preferably, simultaneously therewith, charge is integrated on the second capacitor of each photodiode of the diode array 90. In this regard, when one capacitor is being used for charge storage, the other capacitor is being used for data collection or read out. After charge has been collected at 90, the x-ray source is then moved to a new view position 94. Simultaneously therewith, charge is read out from the second capacitors of each photodiode of the diode array 92. Once the second capacitors have been read out for data collection, both capacitors are grounded so as to bleed out any uncollected residual charge for the next view acquisition 96. Steps 82 through 96 are then repeated throughout the remaining acquisition views.

Figure 9:
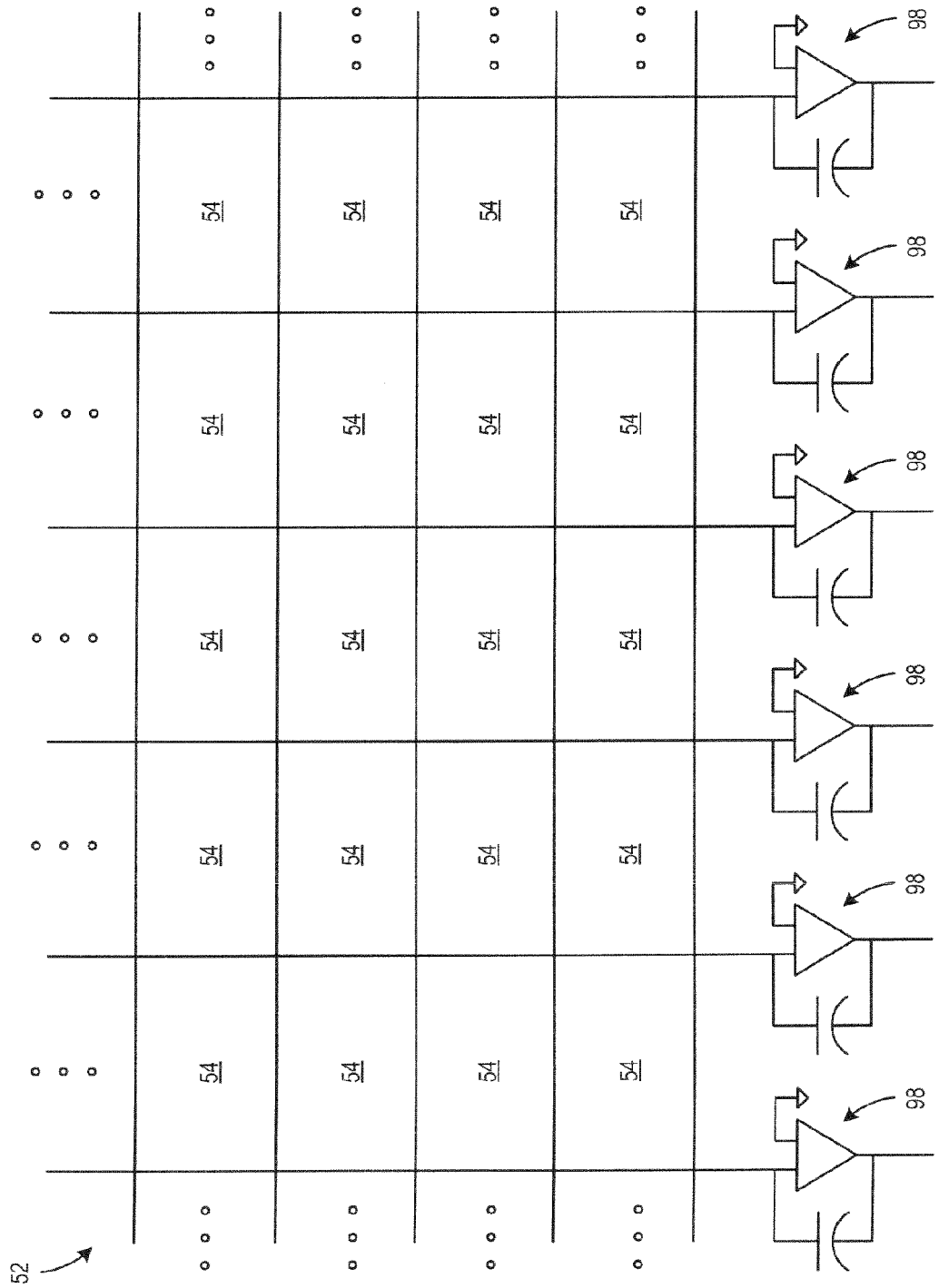
FIG. 9 is a schematic layout of a photodiode array with shared readout channels according to another aspect of the present invention.

Advantageously, the present invention also allows for multiple pixels of a detector array to be connected to a shared readout channel of the system DAS. This is illustrated in FIG. 9. As shown, detector array 52 includes a series of pixels 54. As described previously, each pixel 54 includes multiple charge storage devices that alternately store charge resulting from scintillators releasing light in response to the reception of x-rays. The readout channels are schematically shown as readout amplifiers 98. With this construction, each readout channel 98 sequentially reads out charge from the photodiodes 54 connected thereto. In this regard, the system DAS is capable of reading out data from multiple photodiodes during a given view. For example, if a given view is defined to be one millisecond in length, and the charge stored on each photodiode can be read out in 100 microseconds, then each DAS channel can be connected to read out from 10 pixels. For such an example, the present invention thereby reduces the number of amplifier channels by a factor of 10. Or, conversely, increases the number of possible pixels without increasing the number of DAS channels by a factor of 10. Moreover, as the present invention supports the acquisition of two sets of data per view, the present invention, for the example of a gantry rotation defined to have 1000 views, effectively allows for the acquisition of 2000 views of data in a single gantry rotation with a tenfold decrease in the required number of DAS channels or a tenfold increase in the number of pixels thereby increasing image resolution and sensitivity.

Figure 10:
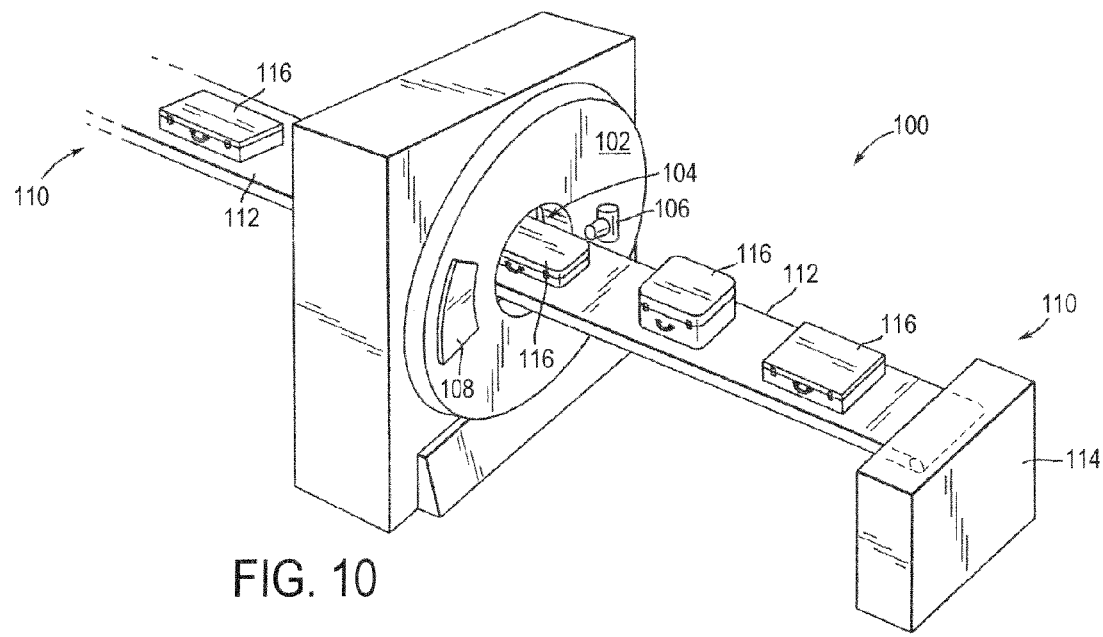
FIG. 10 is a pictorial view of a CT system for use with a non-invasive package inspection system.

Referring now to FIG. 10, package/baggage inspection system 100 includes a rotatable gantry 102 having an opening 104 therein through which packages or pieces of baggage may pass. The rotatable gantry 102 houses an x-ray source 106 as well as a detector assembly 108 having scintillator arrays comprised of scintillator cells. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

Therefore, the invention includes a photodiode having a single light conversion element designed to convert light released by a scintillator to electrical charge. The photodiode also has a first charge storage device connected to the single light conversion element that stores electrical charge during a first acquisition and a second charge storage device different from the first charge storage device, and connected to the single light conversion element that stores electrical charge during a second acquisition.

The present invention has been described in terms of the preferred embodiment, and it is recognized that equivalents, alternatives, and modifications, aside from those expressly stated, are possible and within the scope of the appending claims.

What is claimed is:

1. A CT system comprising:
    an x-ray source capable of wobbling a focal spot to a first source position and to a second source position within a view;
    an x-ray detector having an array of pixels, said detector including a plurality of scintillators arranged to release light to the array of pixels, each pixel comprising a first and a second charge storage device disposed on the pixel surface, the first charge storage device configured to receive a charge generated in a corresponding pixel when the focal spot is wobbled to the first source position, and the second charge storage device configured to receive a charge generated in the corresponding pixel when the focal spot is wobbled to the second source position;
    a DAS connected to receive electrical signals from the array of pixels; and
    a controller configured to alternately connect the first and the second charge storage devices of each of the array of pixels to the DAS such that only one of the first and the second charge storage devices of each pixel collects charge at a time.

2. The CT system of claim 1 wherein the array of pixels comprises frontlit photodiodes.

3. The CT system of claim 1 further comprising a gantry having the x-ray source and the x-ray controller housed therein, and wherein the controller is further configured to:
    segment data acquisition into a number of views;
    partition each view into a first view segment and a second view segment;
    position the x-ray source at a first view position for acquisition of the first view segment; and
    wobble the x-ray source to a second view position for acquisition of the second view segment.

4. The CT system of claim 3 wherein the controller is further configured to connect the first charge device to a charge storage state for the first view segment and connect the second charge storage device to a charge storage state for the second view segment.

5. The CT system of claim 4 wherein the controller is configured to reset the first and to second charge storage devices of the plurality of pixels between acquisition views.

6. The CT system of claim 1 incorporated into at least one of a medical imaging scanner or a baggage/parcel/package inspection scanner.

7. A method of CT imaging comprising the steps of:
    defining data acquisition into a number of views;
    for each view, acquiring CT data at a first x-ray source position and a second x-ray source position wobbled from the first x-ray source position;
    integrating charge from a photodiode to a first charge storage device of a pixel during data acquisition with the x-ray source at the first x-ray source position, wherein the first charge storage device is disposed on the photodiode surface; and
    integrating charge on a second charge storage device of the pixel from the photodiode during data acquisition with the x-ray source at the second x-ray source position, wherein the second charge storage device is disposed on the photodiode surface.

8. The method of claim 7 further comprising the step of reading out charge from one charge storage device during the integration of charge on another charge storage device.

* * * * *